(12) United States Patent
Ching et al.

(10) Patent No.: US 9,050,017 B2
(45) Date of Patent: Jun. 9, 2015

(54) IMPEDANCE ANALYZER

(75) Inventors: Tak-Shing Ching, Taichung (TW);
Tai-Ping Sun, Jhongli (TW); Chia-Ming Liu, Nantou (TW)

(73) Assignee: National Chi Nan University, Nantou (TW)

( * ) Notice: Subject to any disclaimer, the term of this patent is extended or adjusted under 35 U.S.C. 154(b) by 416 days.

(21) Appl. No.: 13/555,616

(22) Filed: Jul. 23, 2012

(65) Prior Publication Data

US 2013/0169296 A1 Jul. 4, 2013

(30) Foreign Application Priority Data

Jan. 4, 2012 (TW) .............................. 101100312 A

(51) Int. Cl.
*A61B 5/053* (2006.01)
*G01R 31/28* (2006.01)
*G01R 27/26* (2006.01)

(52) U.S. Cl.
CPC .................. *A61B 5/053* (2013.01); *G01R 27/26* (2013.01); *G01R 31/2882* (2013.01)

(58) Field of Classification Search
CPC .................................... A61B 5/04; A61B 5/053
See application file for complete search history.

(56) References Cited

U.S. PATENT DOCUMENTS

| | | | |
|---|---|---|---|
| 6,292,690 B1 * | 9/2001 | Petrucelli et al. | 600/547 |
| 6,631,292 B1 * | 10/2003 | Liedtke | 600/547 |
| 7,853,319 B2 * | 12/2010 | Davies | 600/547 |
| 2007/0167879 A1 * | 7/2007 | Cochran | 600/595 |
| 2008/0004904 A1 | 1/2008 | Tran | |
| 2008/0013747 A1 | 1/2008 | Tran | |
| 2010/0249641 A1 * | 9/2010 | Cha | 600/547 |
| 2011/0115624 A1 | 5/2011 | Tran | |
| 2012/0194203 A1 * | 8/2012 | Osawa | 324/663 |

FOREIGN PATENT DOCUMENTS

| | | |
|---|---|---|
| TW | 200635627 A | 10/2006 |
| TW | 201030710 A1 | 8/2010 |

OTHER PUBLICATIONS

Search Report received in Taiwanese Counterpart Application on Oct. 15, 2013, 1 page.

* cited by examiner

*Primary Examiner* — Sean Dougherty
(74) *Attorney, Agent, or Firm* — LeClairRyan

(57) ABSTRACT

An impedance analyzer includes: a control voltage generating unit for generating a control voltage that has a predetermined amplitude value; a measuring unit operable to provide an output current, which has an amplitude value corresponding to that of the control voltage, for flowing through first and second body portions of a biological target, and to generate a measurement voltage that has an amplitude value corresponding to a difference between voltages at the first and second body portions attributed to flow of the output current therethrough; and a calculating module operable to determine an electrical impedance between the first and second body portions according to a predetermined adjustment value and the amplitude value of the measurement voltage.

11 Claims, 3 Drawing Sheets

IMPEDANCE ANALYZER

CROSS-REFERENCE TO RELATED APPLICATION

This application claims priority of Taiwanese Application No. 101100312, filed on Jan. 4, 2012.

BACKGROUND OF THE INVENTION

1. Field of the Invention

The present invention relates to an impedance analyzer, more particularly to an impedance analyzer suitable for analyzing impedance of a biological target.

2. Description of the Related Art

A conventional impedance analyzer, such as model WK6420C available from Dongguan YuanYi Electronics Co., lacks a protection mechanism for limiting constant current. During use, when a current generated by the impedance analyzer is provided through a human body, injury may occur if the current is too large.

SUMMARY OF THE INVENTION

Therefore, an object of the present invention is to provide an impedance analyzer capable of alleviating the aforesaid drawback of the prior art.

Accordingly, an impedance analyzer of the present invention is suitable to be coupled electrically across first and second body portions of a biological target for determining electrical impedance therebetween.

The impedance analyzer includes a readout module and a calculating module.

The readout module includes a control voltage generating unit and a measuring unit. The control voltage is operable to generate a control voltage that has a predetermined amplitude value. The measuring unit is adapted to be coupled electrically across the first and second body portions, is connected electrically to said control voltage generating unit for receiving the control voltage from the control voltage generating unit, and is operable to provide an output current according to the control voltage received by the measuring unit for flowing through the first and second body portions. The output current has an amplitude value that corresponds to the amplitude value of the control voltage received by the measuring unit. The measuring unit is further operable to generate a measurement voltage that has an amplitude value corresponding to a difference between voltages at the first and second body portions attributed to flow of the output current through the first and second body portions.

The calculating module has stored therein a predetermined adjustment value, is connected electrically to the measuring unit for receiving the measurement voltage from the measuring unit, and is operable to determine the electrical impedance between the first and second body portions according to the predetermined adjustment value and the amplitude value of the measurement voltage received by the calculating module.

Another object of the present invention is to provide a readout module suitable to be coupled electrically across first and second body portions of a biological target so as to generate a measurement voltage according to a difference between voltages at the first and second body portions attributed to flow of an output current through the first and second body portions.

Accordingly, a readout module of the present invention includes a control voltage generating unit and a measuring unit.

The control voltage generating unit is operable to generate a control voltage that has a predetermined amplitude value.

The measuring unit is adapted to be coupled electrically across the first and second body portions, is connected electrically to the control voltage generating unit for receiving the control voltage from the control voltage generating unit, and is operable to provide the output current according to the control voltage received by the measuring unit for flowing through the first and second body portions. The output current has an amplitude value that corresponds to the amplitude value of the control voltage received by the measuring unit. The measuring unit is further operable to generate the measurement voltage that has an amplitude value corresponding to the difference between the voltages at the first and second body portions.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
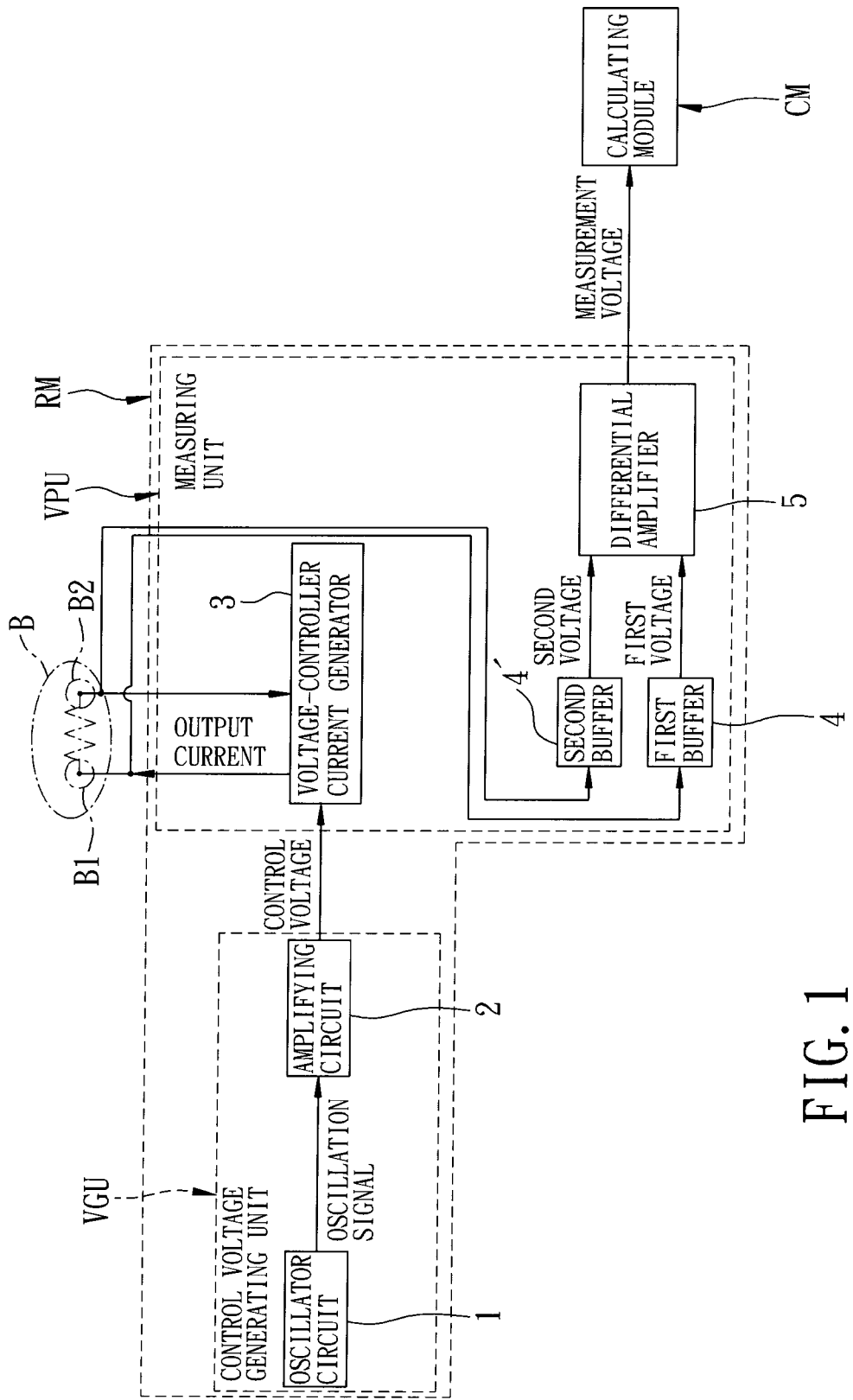
FIG. 1 is a circuit block diagram to illustrate the preferred embodiment of an impedance analyzer according to the present invention.

Referring to FIG. 1, the preferred embodiment of an impedance analyzer according to the present invention is suitable to be coupled electrically across first and second body portions (B1, B2) of a biological target (B) for determining electrical impedance therebetween, and includes a readout module (RM) and an calculating module (CM) operatively associated with the readout module (RM).

The readout module (RM) includes a control voltage generating unit (VGU) operable to generate an alternating-current (AC) control voltage that has a predetermined amplitude value. In this embodiment, the control voltage generating unit (VGU) includes an oscillator circuit 1 operable for generating an oscillation signal, and an amplifying circuit 2 connected electrically to the oscillator circuit 1 for receiving the oscillation signal from the oscillator circuit 1 and for amplifying the oscillation signal so as to generate the control voltage.

Figure 2:
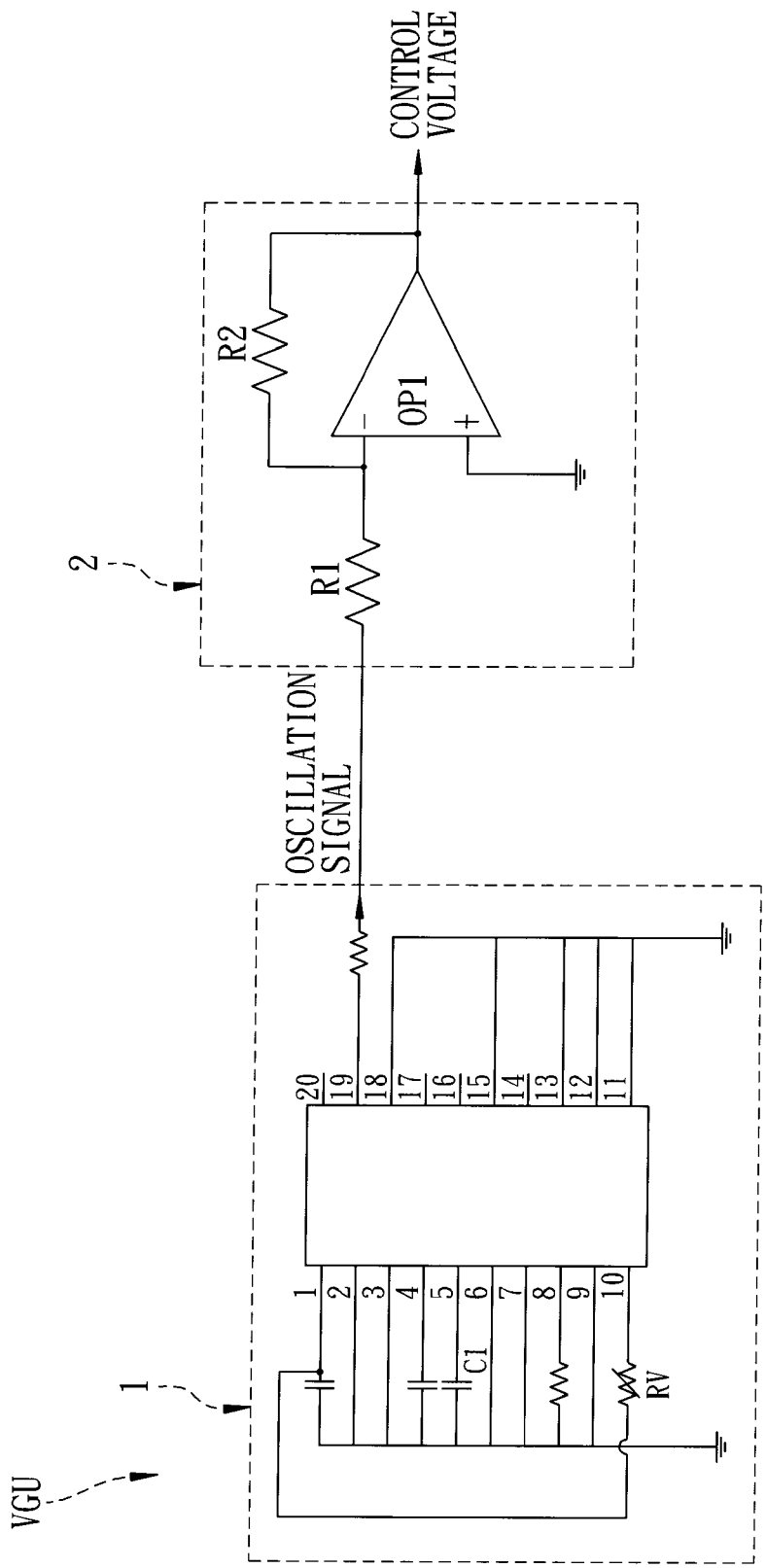
FIG. 2 is a circuit block diagram to illustrate a control voltage generating unit of a readout module of the impedance analyzer.

In this embodiment, the oscillation signal thus generated has an amplitude value of 2V, ranging from −1V to 1V, and has a frequency adjustable between the range of 0.1 MHz to 20 MHz via a variable resistor RV (see FIG. 2).

Referring to FIG. 2, the amplifying circuit 2 includes a first operational amplifier (OP1), a first resistor (R1), and a second resistor (R2). The first operational amplifier (OP1) has an inverting input terminal connected electrically to the oscillator circuit 1 via the first resistor (R1) for receiving the oscillation signal therefrom, a grounded non-inverting input terminal, and an output terminal connected electrically to the inverting input terminal via the second resistor (R2). The first operational amplifier (OP1) is operable to generate the control voltage for output via the output terminal thereof. The control voltage thus generated has an amplitude value corresponding to an absolute value of a result of product of the amplitude value of the oscillation signal and a resistance of the second resistor (R2) divided by a resistance of the first resistor (R1).

Referring once more to FIG. 1, the readout module (RM) further includes a measuring unit (VPU) connected electrically to the control voltage generating unit (VGU) for receiving the control voltage therefrom, and operable to provide an output current according to the control voltage received by the readout module (RM) for flowing through the first and second body portions (B1, B2) of the biological target (B). The output current has an amplitude value varying in a positive relation to the predetermined amplitude value of the control voltage.

The measuring unit (VPU) includes a voltage-controlled current generator 3, first and second buffers 4, 4', and a differential amplifier 5.

Figure 3:
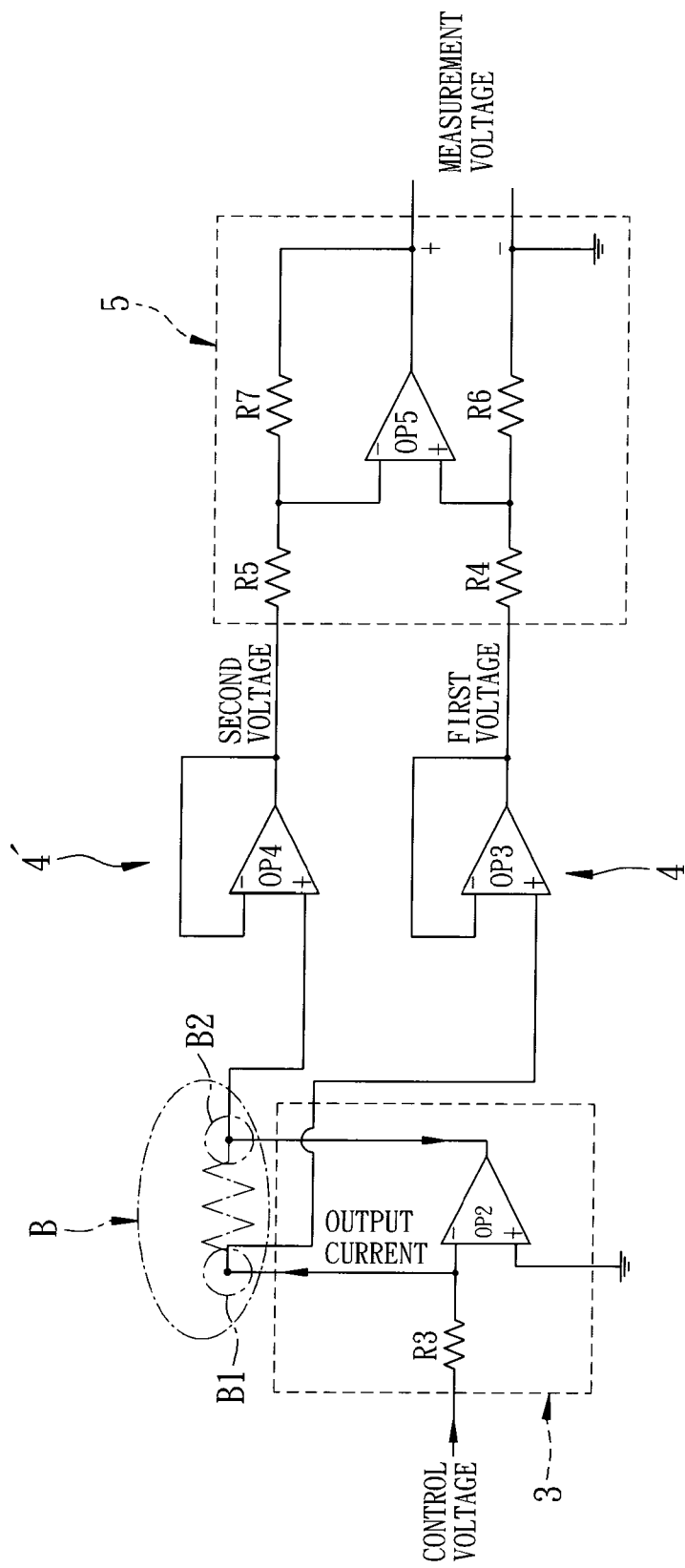
FIG. 3 is a circuit block diagram to illustrate a measuring unit of the readout module.

Referring to FIG. 3, the voltage-controlled current generator 3 includes a second operational amplifier (OP2) and a third resistor (R3). The second operational amplifier (OP2) has an inverting input terminal that is connected electrically to the amplifying circuit 2 via the third resistor (R3) for receiving the control voltage therefrom and that is adapted to be coupled electrically to the first body portion (B1), a grounded non-inverting input terminal, and an output terminal that is adapted to be coupled electrically to the second body portion (B2). A current flowing through the third resistor (R3) serves as the output current.

In this embodiment, the amplitude value of the output current corresponds to a result of division of the amplitude value of the control voltage by a resistance of the third resistor (R3). Since the amplitude value of the control voltage is predetermined, the amplitude value of the output current is also predetermined.

The first and second buffers 4, 4' include third and fourth operational amplifiers (OP3, OP4), respectively.

The third operational amplifier (OP3) has a non-inverting input terminal connected electrically to the inverting input terminal of the second operational amplifier (OP2), an inverting input terminal, and an output terminal connected electrically to the inverting input terminal of the third operational amplifier (OP3). The third operational amplifier (OP3) is operable to generate a first voltage, according to a voltage at the inverting input terminal of the second operational amplifier (OP2), for output via the output terminal thereof. The first voltage thus generated has an amplitude value corresponding to the amplitude value of the voltage at the first body portion (B1).

The fourth operational amplifier (OP4) has a non-inverting input terminal connected electrically to the output terminal of the second operational amplifier (OP2), an inverting input terminal, and an output terminal connected electrically to the inverting input terminal of the fourth operational amplifier (OP4). The fourth operational amplifier (OP4) is operable to generate a second voltage, according to a voltage at the output terminal of the second operational amplifier (OP2), for output via the output terminal thereof. The second voltage thus generated has an amplitude value corresponding to the amplitude value of the voltage at the second body portion (B2).

The differential amplifier 5 is connected electrically to the output terminal of each of the third and fourth operational amplifiers (OP4, OP5) for receiving a corresponding one of the first and second voltages therefrom, and is operable to generate a measurement voltage having an amplitude value that varies in a positive relation to a difference between the first and second voltages received by the differential amplifier 5.

In this embodiment, the differential amplifier 5 includes fourth, fifth, sixth, and seventh resistors (R4-R7), and a fifth operational amplifier (OP5) having: an inverting input terminal that is connected electrically to the output terminal of the fourth operational amplifier (OP4) via the fifth resistor (R5) for receiving the second voltage therefrom; a non-inverting input terminal that is connected electrically to the output terminal of the third operational amplifier (OP3) via the fourth resistor (R4) for receiving the first voltage therefrom, and that is connected electrically to ground via the sixth resistor (R6); and an output terminal that is connected electrically to the inverting input terminal of the fifth operational amplifier (OP5) via the seventh resistor (R7). The fifth operational amplifier (OP5) is operable to generate the measurement voltage for output via the output terminal thereof according to the first and second voltages received by the fifth operational amplifier (OP5).

The differential amplifier 5 has a gain corresponding to a result of division of a resistance of the seventh resistor (R7) by that of the fifth resistor (R5), which is substantially equal to a result of division of a resistance of the sixth resistor (R6) by that of the fourth resistor (R4), and which, in this embodiment, is equal to two. The amplitude value of the measurement voltage corresponds substantially to a result of division of the difference between the first and second voltages by the gain of the differential amplifier 5.

Since the amplitude value of the output current is predetermined, the calculating module (CM) may be preconfigured with a predetermined adjustment value corresponding to the predetermined amplitude value of the output current for later comparison with the amplitude value of the measurement voltage outputted by the measuring unit (VPU) so as to determine the electrical impedance between the first and second body portions (B1, B2). In particular, the impedance value thus determined corresponds to a result of division of the difference between the first and second voltages by the predetermined adjustment value.

In summary, since the amplitude value of the output current varies in a positive relation with the predetermined amplitude value of the control voltage, the amplitude value of the output current does not vary according to the electrical impedance of the biological target (B), thereby reducing the risk of injury to the biological target (B).

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. An impedance analyzer suitable to be coupled electrically across first and second body portions of a biological target for determining electrical impedance therebetween, comprising:

a readout module including
 a control voltage generating unit operable to generate a control voltage that has a predetermined amplitude value, and including
 an oscillator circuit operable for generating an oscillation signal, and
 an amplifying circuit that is connected electrically to said oscillator circuit for receiving the oscillation signal from said oscillator circuit, and that is operable to generate the control voltage based on the oscillation signal received by said amplifying circuit, a measuring unit adapted to be coupled electrically across the first and second body portions, connected electrically to said control voltage generating unit for receiving the control voltage from said control voltage generating unit, and operable to provide an output current according to the control voltage received by said measuring unit for flowing through the first and second body portions, the output current having an amplitude value that corresponds to the amplitude value of the control voltage received by said measuring unit, said measuring unit being further operable to generate a measurement voltage that has an amplitude value corresponding to a difference between voltages at the first and second body portions attributed to flow of the output current through the first and second body portions; and a calculating module having stored therein a predetermined adjustment value, connected electrically to said measuring unit for receiving the measurement voltage from said measuring unit, and operable to determine the electrical impedance between the first and second body portions according to the predetermined adjustment value and the amplitude value of the measurement voltage received by said calculating module;

wherein said amplifying circuit includes
first and second resistors, and
a first operational amplifier having a first input terminal that is connected electrically to said oscillator circuit via said first resistor for receiving the oscillation signal from said oscillator circuit, a grounded second input terminal, and an output terminal that is connected electrically to said first input terminal of said first operational amplifier via said second resistor, said first operational amplifier being operable to generate the control voltage for output via said output terminal thereof.

2. The impedance analyzer as claimed in claim 1, wherein said measuring unit includes:

a voltage-controlled current generator connected electrically to said control voltage generating unit for receiving the control voltage from said control voltage generating unit, operable to generate the output current according to the control voltage received by said voltage-controlled current generator, and adapted to be coupled electrically across the first and second body portions for providing the output current for flowing through the first and second body portions;

first and second buffers adapted to be coupled electrically to the first and second body portions for receiving the voltages at the first and second body portions, and operable to output first and second voltages according to the voltages received by said first and second buffers, respectively; and a differential amplifier connected electrically to said first and second buffers for receiving the first and second voltages from said first and second buffers, respectively, and operable to output the measurement voltage according to the first and second voltages received by said differential amplifier, the amplitude value of the measurement voltage corresponding to a difference between the first and second voltages received by said differential amplifier.

3. The impedance analyzer as claimed in claim 2, wherein said voltage-controlled current generator includes:

a third resistor; and
a second operational amplifier having a first input terminal that is connected electrically to said control voltage generating unit via said third resistor for receiving the control voltage from said control voltage generating unit and that is adapted to be coupled electrically to the first body portion, a grounded second input terminal, and an output terminal that is adapted to be coupled electrically to the second body portion, a current flowing through said third resistor serving as the output current.

4. The impedance analyzer as claimed in claim 3, wherein:

said first buffer includes a third operational amplifier having a first input terminal, a second input terminal that is connected electrically to said first input terminal of said second operational amplifier, and an output terminal that is connected electrically to said first input terminal of said third operational amplifier, said third operational amplifier being operable to generate the first voltage corresponding to the voltage at the first body portion for output via said output terminal of said third operational amplifier, the first voltage having an amplitude value corresponding to the amplitude value of the voltage at the first body portion; and said second buffer includes a fourth operational amplifier having a first input terminal, a second input terminal that is connected electrically to said output terminal of said second operational amplifier, and an output terminal that is connected electrically to said first input terminal of said fourth operational amplifier, said fourth operational amplifier being operable to generate the second voltage corresponding to the voltage at the second body portion for output via said output terminal of said fourth operational amplifier, the second voltage having an amplitude value corresponding to the amplitude value of the voltage at the second body portion.

5. The impedance analyzer as claimed in claim 4, wherein said differential amplifier includes:

fourth, fifth, sixth, and seventh resistors; and
a fifth operational amplifier having
a first input terminal connected electrically to said output terminal of one of said third and fourth operational amplifiers via said fifth resistor for receiving a corresponding one of the first and second voltages from said one of said third and fourth operational amplifiers,
a second input terminal connected electrically to said output terminal of the other of said third and fourth operational amplifiers via said fourth resistor for receiving a corresponding one of the first and second voltages from the other of said third and fourth operational amplifiers, and connected electrically to ground via said sixth resistor, and
an output terminal connected electrically to said first input terminal of said fifth operational amplifier via said seventh resistor, said fifth operational amplifier being operable to generate the measurement voltage for output via said output terminal thereof according to the first and second voltages received thereby.

6. The impedance analyzer as claimed in claim 1, wherein the predetermined adjustment value corresponds to the amplitude value of the output current generated by said measuring unit.

7. A readout module suitable to be coupled electrically across first and second body portions of a biological target so as to generate a measurement voltage according to a difference between voltages at the first and second body portions attributed to flow of an output current through the first and second body portions, said readout module comprising:

a control voltage generating unit operable to generate a control voltage that has a predetermined amplitude value; and including
an oscillator circuit operable for generating an oscillation signal, and
an amplifying circuit that is connected electrically to said oscillator circuit for receiving the oscillation signal from said oscillator circuit, and that is operable to generate the control voltage based on the oscillation signal received by said amplifying circuit; and
a measuring unit adapted to be coupled electrically across the first and second body portions, connected electrically to said control voltage generating unit for receiving the control voltage from said control voltage generating unit, and operable to provide the output current according to the control voltage received by said measuring unit for flowing through the first and second body portions, the output current having an amplitude value that corresponds to the amplitude value of the control voltage received by said measuring unit, said measuring unit being further operable to generate the measurement voltage that has an amplitude value corresponding to the difference between the voltages at the first and second body portions;
wherein said amplifying circuit includes
first and second resistors, and
a first operational amplifier having a first input terminal that is connected electrically to said oscillator circuit via said first resistor for receiving the oscillation signal from said oscillator circuit, a grounded second input terminal, and an output terminal that is connected electrically to said first input terminal of said first operational amplifier via said second resistor, said first operational amplifier being operable to generate the control voltage for output via said output terminal thereof.

8. The readout module as claimed in claim 7, wherein said measuring unit includes:
a voltage-controlled current generator connected electrically to said control voltage generating unit for receiving the control voltage from said control voltage generating unit, operable to generate the output current according to the control voltage received by said voltage-controlled current generator, and adapted to be coupled electrically across the first and second body portions for providing the output current for flowing through the first and second body portions;
first and second buffers adapted to be coupled electrically to the first and second body portions for receiving the voltages at the first and second body portions, and operable to output first and second voltages according to the voltages received by said first and second buffers, respectively; and
a differential amplifier connected electrically to said first and second buffers for receiving the first and second voltages from said first and second buffers, respectively, and operable to output the measurement voltage according to the first and second voltages received by said differential amplifier, the amplitude value of the measurement voltage corresponding to a difference between the first and second voltages received by said differential amplifier.

9. The readout module as claimed in claim 8, wherein said voltage-controlled current generator includes:

a third resistor; and
a second operational amplifier having a first input terminal that is connected electrically to said control voltage generating unit via said third resistor for receiving the control voltage from said control voltage generating unit and that is adapted to be coupled electrically to the first body portion, a grounded second input terminal, and an output terminal that is adapted to be coupled electrically to the second body portion, a current flowing through said third resistor serving as the output current.

10. The readout module as claimed in claim 9, wherein:
said first buffer includes a third operational amplifier having a first input terminal, a second input terminal that is connected electrically to said first input terminal of said second operational amplifier, and an output terminal that is connected electrically to said first input terminal of said third operational amplifier, said third operational amplifier being operable to generate the first voltage corresponding to the voltage at the first body portion for output via said output terminal of said third operational amplifier, the first voltage having an amplitude value corresponding to the amplitude value of the voltage at the first body portion; and
said second buffer includes a fourth operational amplifier having a first input terminal, a second input terminal that is connected electrically to said output terminal of said second operational amplifier, and an output terminal that is connected electrically to said first input terminal of said fourth operational amplifier, said fourth operational amplifier being operable to generate the second voltage corresponding to the voltage at the second body portion for output via said output terminal of said fourth operational amplifier, the second voltage having an amplitude value corresponding to the amplitude value of the voltage at the second body portion.

11. The readout module as claimed in claim 10, wherein said differential amplifier includes:
fourth, fifth, sixth, and seventh resistors; and
a fifth operational amplifier having
a first input terminal connected electrically to said output terminal of one of said third and fourth operational amplifiers via said fifth resistor for receiving a corresponding one of the first and second voltages from said one of said third and fourth operational amplifiers,
a second input terminal connected electrically to said output terminal of the other of said third and fourth operational amplifiers via said fourth resistor for receiving a corresponding one of the first and second voltages from the other of said third and fourth operational amplifiers, and connected electrically to ground via said sixth resistor, and
an output terminal connected electrically to said first input terminal of said fifth operational amplifier via said seventh resistor, said fifth operational amplifier being operable to generate the measurement voltage for output via said output terminal thereof according to the first and second voltages received thereby.

* * * * *